United States Patent [19]

Hines et al.

[11] Patent Number: 5,606,133

[45] Date of Patent: *Feb. 25, 1997

[54] GYRATORY COMPACTOR WITH MOLD SPECIMEN EXTRUDER

[75] Inventors: Theodore G. Hines, Grove City; Roger A. Pyle, Clarion, both of Pa.

[73] Assignee: Pine Instrument Company, Grove City, Pa.

[*] Notice: The term of this patent shall not extend beyond the expiration date of Pat. No. 5,456,118.

[21] Appl. No.: 540,398

[22] Filed: Oct. 6, 1995

[51] Int. Cl.$^6$ .................................................. G01N 3/08
[52] U.S. Cl. .................................. 73/824; 73/818; 73/843
[58] Field of Search .............................. 73/824, 825, 822, 73/820, 843, 85, 818, 865.3, 866

[56] References Cited

U.S. PATENT DOCUMENTS

| | | | |
|---|---|---|---|
| 2,737,805 | 3/1956 | Blumenbaum | 73/843 |
| 2,972,249 | 2/1961 | McRae et al. | 73/795 |
| 4,616,508 | 10/1986 | Jörn | 73/825 |
| 4,942,768 | 7/1990 | McRae | 73/795 |
| 5,036,709 | 8/1991 | McRae | 73/841 |
| 5,323,655 | 6/1994 | Eagan et al. | 73/84 |
| 5,456,118 | 10/1995 | Hines et al. | 73/843 |

Primary Examiner—Richard Chilcot
Assistant Examiner—Max H. Noori
Attorney, Agent, or Firm—Calfee Halter & Griswold

[57] ABSTRACT

A gyratory compacting and mold extruding apparatus for compacting a specimen of material within a mold as the mold is gyrated includes a frame for supporting a mold, a mold gyrating carriage, a compaction ram and ram driving assembly, and a mold specimen extruder. The mold gyrating carriage receives a cylindrical mold having a cavity for holding material and an external peripheral flange about which the mold carriage is guided and driven to gyrate the mold while the ram is drivingly inserted through the open top of the mold. The ram driving assembly is supported by a flexible portion of the frame which flexes in reaction to force transferred by the ram. Strain gauges on the flexible portion of the frame provide feedback control data on ram force to an integrated computer control system which selectively controls the ram driving assembly to control the force transferred by the ram at least partially according to data generated by the strain gauges. The energy required to rotate the mold gyrating carriage around the mold is measured. A mold specimen extruder is provided on a common plane with the surface which supports the mold for gyration and compaction. An extrusion rod is powered to rise vertically through the bottom of the mold to extrude compacted material from the mold.

12 Claims, 11 Drawing Sheets

SPECIMEN HEIGHT (mm) vs. GYRATION NO.

Date: 12/20/93
Time: 13:40

| | 0 | 1 | 2 | 3 | 4 | 5 | 6 | 7 | 8 | 9 |
|---|---|---|---|---|---|---|---|---|---|---|
| 0 | 126.0 | 122.2 | 120.3 | 118.8 | 117.8 | 116.9 | 116.1 | 115.5 | 114.9 | 114.4 |
| 10 | 113.9 | 113.5 | 113.1 | 112.8 | 112.5 | 112.2 | 111.9 | 111.6 | 111.4 | 111.2 |
| 20 | 111.0 | 110.8 | 110.6 | 110.4 | 110.2 | 110.0 | 109.9 | 109.7 | 109.6 | 109.4 |
| 30 | 109.3 | 109.2 | 109.0 | 108.9 | 108.8 | 108.7 | 108.6 | 108.5 | 108.4 | 108.3 |
| 40 | 108.2 | 108.1 | 108.0 | 107.9 | 107.8 | 107.8 | 107.7 | 107.6 | 107.5 | 107.4 |
| 50 | 107.4 | 107.3 | 107.2 | 107.2 | 107.1 | 107.0 | 107.0 | 106.9 | 106.9 | 106.8 |
| 60 | 106.8 | 106.7 | 106.7 | 106.6 | 106.6 | 106.5 | 106.5 | 106.4 | 106.4 | 106.3 |
| 70 | 106.3 | 106.2 | 106.2 | 106.1 | 106.1 | 106.1 | 106.0 | 106.0 | 105.9 | 105.9 |
| 80 | 105.9 | 105.8 | 105.8 | 105.8 | 105.7 | 105.7 | 105.6 | 105.6 | 105.6 | 105.5 |
| 90 | 105.5 | 105.5 | 105.4 | 105.4 | 105.4 | 105.3 | 105.3 | 105.3 | 105.3 | 105.2 |
| 100 | 105.2 | 105.2 | 105.2 | 105.1 | 105.1 | 105.1 | 105.1 | 105.0 | 105.0 | 105.0 |
| 110 | 105.0 | 104.9 | 104.9 | 104.9 | 104.9 | 104.8 | 104.8 | 104.8 | 104.8 | 104.8 |
| 120 | 104.7 | 104.7 | 104.7 | 104.7 | 104.7 | 104.6 | 104.6 | 104.6 | 104.6 | 104.5 |
| 130 | 104.5 | 104.5 | 104.5 | 104.5 | 104.5 | 104.5 | 104.4 | 104.4 | 104.4 | 104.4 |
| 140 | 104.4 | 104.3 | 104.3 | 104.3 | 104.3 | 104.3 | 104.3 | 104.2 | 104.2 | 104.2 |
| 150 | 104.2 | 104.2 | 104.2 | 104.1 | 104.1 | 104.1 | 104.1 | 104.1 | 104.1 | 104.0 |
| 160 | 104.0 | 104.0 | 104.0 | 104.0 | 104.0 | 104.0 | 103.9 | 103.9 | 103.9 | 103.9 |
| 170 | 103.9 | 103.9 | 103.9 | 103.9 | 103.8 | 103.8 | 103.8 | 103.8 | 103.8 | 103.8 |
| 180 | 103.8 | 103.8 | 103.8 | 103.8 | 103.7 | 103.7 | 103.7 | 103.7 | 103.7 | 103.7 |
| 190 | 103.7 | 103.7 | 103.7 | 103.6 | 103.6 | 103.6 | 103.6 | 103.6 | 103.6 | 103.6 |
| 200 | 103.6 | | | | | | | | | |

SAMPLE NO.: ______
SAMPLE SIZE: 150 mm
PRESSURE: 0.40 MPa
FINAL HT.: 103.4 mm
WEIGHT: ______
VOLUME: ______
SPEC. GRAV.: ______
VOIDS: ______
AGGREGATE: ______
GRADE ASPHALT: ______
% ASPHALT: ______
TEMPERATURE: ______

PASSING
200 ______
100 ______
50 ______
30 ______
16 ______
8 ______
4 ______
3/8 ______
1/2 ______
3/4 ______
1-1/2 ______

LAB. NO.: ______
REPORT BY: ______

| | No. Gyr. | % Air Voids |
|---|---|---|
| Init.: | ____ | ____ |
| Design: | ____ | ____ |
| Final: | ____ | ____ |

GYRATORY COMPACTOR WITH MOLD SPECIMEN EXTRUDER

FIELD OF THE INVENTION

The present invention relates generally to a method and apparatus for testing materials and, in particular, to a method and apparatus for testing paving materials by compaction and gyration.

BACKGROUND OF THE INVENTION

Materials testing machines for simulating actual forces upon materials, such as the forces of vehicular traffic upon an asphalt surface of a road bed, have been devised to produce a sample of material which evidences the physical effects of repeated loading by for example compression, compaction, shear strain, plane-strain, and thermal reactivity. Such machines typically include a material holding mold which is inserted into a chamber or carriage which positions the mold for insertion of a ram into the mold cavity to compress the material in the mold. The mold may be gyrated about a small angle relative to the vertical axis of the ram, by motion of the mold carriage, as the material is compressed by the ram to simulate actual forces on the material in the application environment.

U.S. Pat. No. 2,972,249 discloses a kneader compactor which uses opposed plungers to compress materials within a mold chuck mounted for gyratory oscillation to produce kneading stresses in the material in the mold. Gyration of the mold as the material is compressed produces relative motion of particles of the material which simulates the physical response of asphalt material to vehicle load forces.

U.S. Pat. Nos. 4,942,768 and 5,036,709 disclose a paving material testing machine in which paving material to be tested is placed in a mold held by a chuck which is gyrated about a vertical axis while the material is compressed in the mold from the bottom by a hydraulically driven ram. As the mold chuck is rotated, a portion of the mold chuck in contact with the mold dynamically influences the axially adjustable chuck so that deformation of the material within the mold induced by the gyration changes the angle of gyration. This subjects the material in the mold to a gyratory kneading action analogous to the forces exerted by vehicles moving over asphalt surfaces. The machine also performs cyclic vertical loading by timed control of predetermined applied forces of the hydraulic ram upon the sample to simulate the flexing forces of vehicle tires rolling upon the asphalt surface.

Accurate calibration, control and monitoring of the compressive load of the ram upon a sample within the mold as the mold is gyrated is critical to obtaining accurate test results, i.e., compacted specimens which have specified densities, substantially uniform alignment of aggregate materials mixed with the specimen, and elastic properties which closely approximate real world applications. Precise control of the linear travel and compressive force of hydraulically driven rams in compaction devices requires the use of comparatively expensive control components. Also, hydraulic systems are heat sensitive and require frequent maintenance of seals and fluid.

The angle of gyration of the mold during compaction is also a critical factor which determines the amount of kneading action with resultant shear stress and strain of the material within the mold. Although the prior art devices induce kneading action of the material within the mold, the angle of gyration as determined by the density and flow of the material adds a variable which complicates accurate interpretation of the test results. Prior gyratory compaction testing machines do not provide for a precisely fixable and adjustable angle of gyration.

Automated control and safety of operation of gyratory compactors, each vital to obtaining accurate tests results without extensive operator training, are features not adequately addressed in the design of prior machines.

SUMMARY OF THE INVENTION

The present invention provides an improved apparatus and method for preparing a specimen of compressed material by gyratory compaction wherein the angle of gyration is precisely fixed, and the compressive force of the compaction ram upon the material is precisely determinable and controlled throughout the compaction process. The operations of the gyratory compactor of the present invention are controlled by a fully integrated computer control system which controls compaction pressure, gyration cycles and rate, and ram travel to produce compacted material specimens by a predetermined number of gyration cycles or a predetermined compacted specimen height. A stepping motor/load beams feedback drive system integral with a lead screw driven compaction ram provides precision linear control of ram travel and pressure relative to the specimen to be compacted. A completely enclosed compacting chamber and simplified control panel allow the compactor to be safely operated and without extensive operator training.

In accordance with one aspect of the invention, a materials testing apparatus for subjecting a material to forces is provided which includes a mold for containing a quantity of material, a mold supporting frame in contact with a rotatable mold carriage also supported by the frame and connected to a mold carriage tilt assembly operative to lift a portion of the mold carriage to incline the vertical axis of the mold, means for rotating the mold carriage about the mold, and a material compaction ram connected to a ram driving assembly and drivingly insertable into the mold for exerting a compressive force upon material within the mold while the mold carriage is rotated about the mold.

In accordance with another aspect of the invention a gyratory compaction apparatus for subjecting a material to forces is provided which includes a mold having a mold cavity for receiving a quantity of material, the mold having an open top and a closed bottom, a ram axially inserted and driven into the mold cavity through the open top of the mold to compact the material in the mold cavity, and means for gyrating the mold while the ram is inserted and driven into the mold cavity.

In accordance with another aspect of the invention a material testing machine for applying a linear force to a material to be tested is provided which includes a frame for supporting a guide for a ram, said ram driven for linear movement in said guide by an electrically powered motor, load beams as an integral part of the frame and supporting the ram driving lead screw, the load beams being flexible in reaction to forces transferred by the ram, means for measuring an amount of flexing of the load beams, and means for controlling a speed of the ram drive motor in response to measured values of flexion of the load beams.

To the accomplishment of the foregoing and related ends, the invention comprises the features hereinafter fully described and particularly pointed out in the following detailed description made with references to the annexed drawings which set forth in detail certain illustrative embodiments of the invention, these being indicative, however, of but a few of the various ways in which the invention may be employed.

BRIEF DESCRIPTION OF THE DRAWINGS

In the annexed drawings:

FIG. 7 is a representation of a printout of compaction data acquired by the gyratory compactor control system of the present invention, and FIGS. 8A and 8B combined a schematic control diagram of the electronic computer control system of the gyratory compactor of the present invention.

DESCRIPTION OF PREFERRED EMBODIMENTS

Figure 1A:
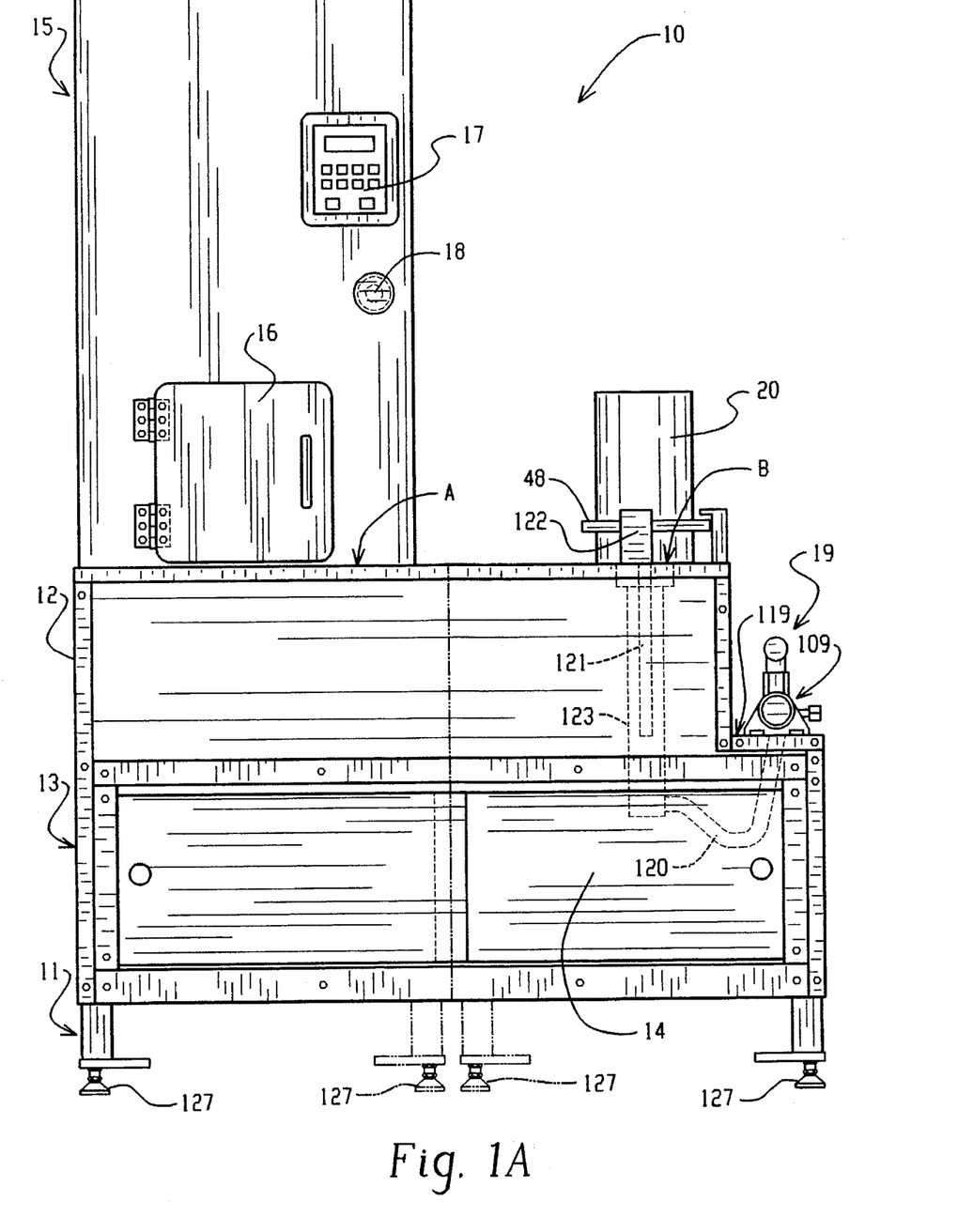
FIG. 1A is a front elevation of a gyratory compactor of the present invention.
Figure 1B:
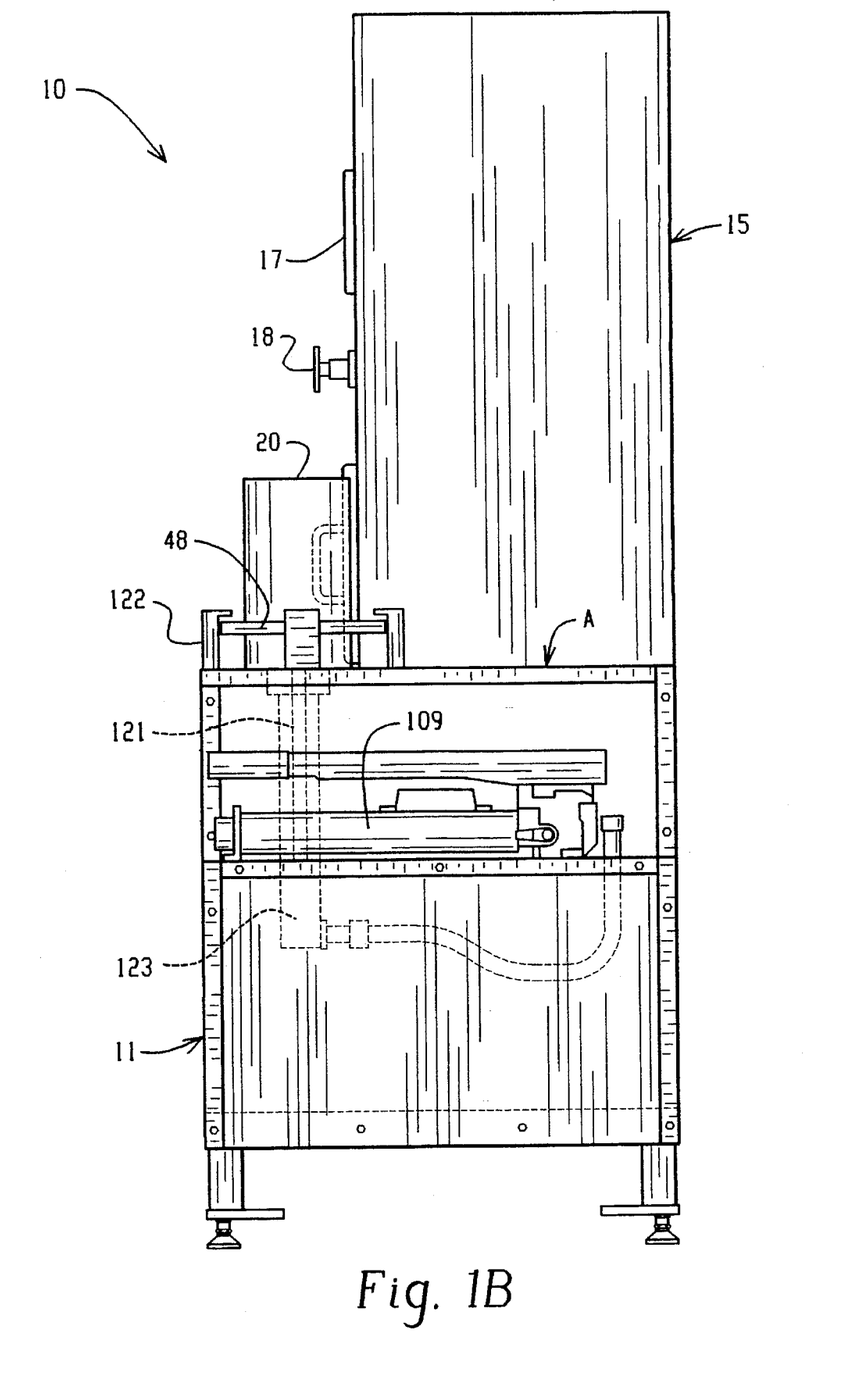
FIG. 1B is a side elevation of a gyratory compactor of the present invention.

FIGS. 1A and 1B illustrate the frame and exterior housing of the gyratory compactor of the present invention indicated generally at 10. A frame 11 supports the compactor and peripheral components such as in this particular embodiment a mold specimen extruder, housed in protective a cabinet 12 attached to the frame. The frame 11 includes a lower portion 13 and an upper specimen mold receiving portion 15. The mold receiving portion 15 includes a first mold supporting surface A, an access door 16, a control panel 17 for controlling the operations of the compactor, and an emergency stop button 18. The lower portion 13 includes access doors 14, a mold specimen extruder support surface 119, and a second mold supporting surface B. A mold specimen extruder (also referred to herein equivalently as an "extruder", "extractor", "specimen extractor" or "material extractor"), indicated generally at 19, for extruding or extracting a compacted specimen from a mold 20, is in this embodiment mounted in lower portion 13 of frame 11 to protrude from the second mold supporting surface B which is in the same plane as the first mold supporting surface A on which the bottom of a mold 20 is supported within mold receiving portion 15 as further described below.

Figure 1C:
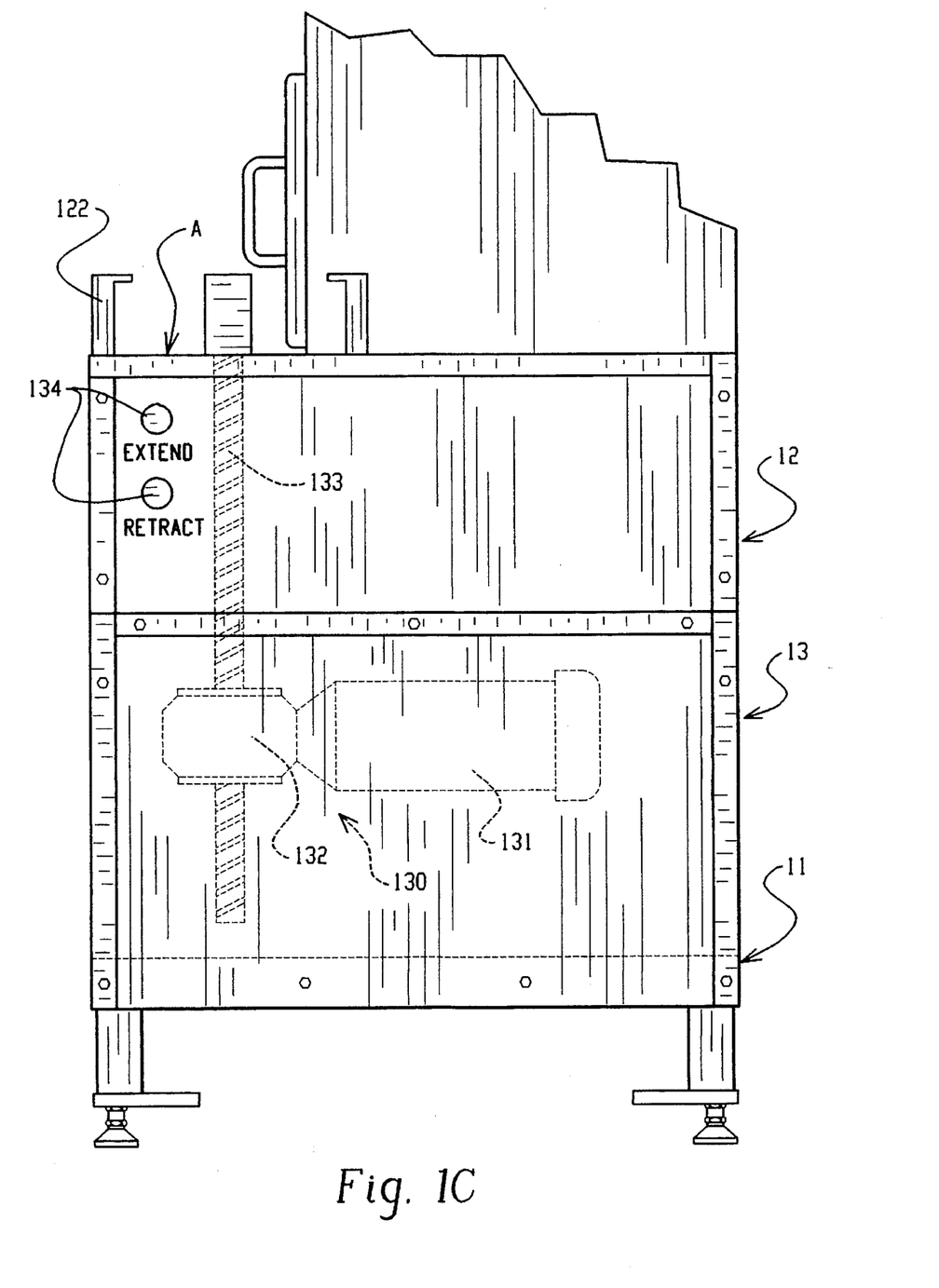
FIG. 1C is a side elevation of an alternate embodiment of a gyratory compactor of the present invention.

As further shown in FIGS. 1A, 1B and 1C, the extruder 19 may be, for example, a hand actuated hydraulic pump 109, such as a Power Team Model No. P-59 manufactured by SPX Corporation, mounted upon frame 13 and connected by line 120 to a hydraulic pump 123 to hydraulically vertically actuate an extruder rod 121 mounted within frame 11 to rise from surface B into a mold 20 held in a position upon surface B generally aligned with the vertical axis of extruder rod 121 (for example by mold positioning extruder brackets 122) whereby the extruder rod extrudes a compacted specimen out of the open top of the mold 20 upon actuation of the hand pump 109. An unobvious advantage of this novel arrangement and combination of gyration compaction machinery and mold specimen extruder is the ease with which a mold can be removed from the compaction machinery and placed in position for power-assisted extrusion of the specimen from the mold immediately proximate to and on the same mold-supporting surface. In other words, the mold does not have to be lifted to move it from the compaction machinery to the extruder. This novel aspect of the invention is particularly advantageous in view of the facts that the weight of a specimen-filled mold is substantial and the external temperature of the mold at completion of a compaction operation is high. As shown in phantom in FIG. 1A, in an alternate embodiment the lower portion 13 of frame 11 which supports second mold supporting surface B can be formed separate from the frame which supports mold supporting surface A, whereby the lower portion 13 is divisible. Vertically adjustable stands 127 allow support surfaces A and B to be precisely positioned in the same plane.

FIG. 1C illustrates an alternate embodiment of the built-in extruder aspect of the invention wherein an electrically powered screw jack assembly, indicated generally at 130 and including a motor 131, gear box 132 and screw 133, is mounted within lower portion 13 of frame 11 to drive vertically oriented screw 133 (also referred to herein as an extruder rod) upward through second mold supporting surface B at the approximate axial center of a mold positioned within mold positioning extruder brackets 122 to extrude a specimen from a mold. The mold positioning extruder brackets 122 fit over a radial flange 48 of mold 20 to retain the mold against surface B as the extruder rod is driven vertically upward into the mold. Power controls 134 for extending and retracting the electric screw jack extruder are mounted on the exterior of cabinet 12.

Figure 2:
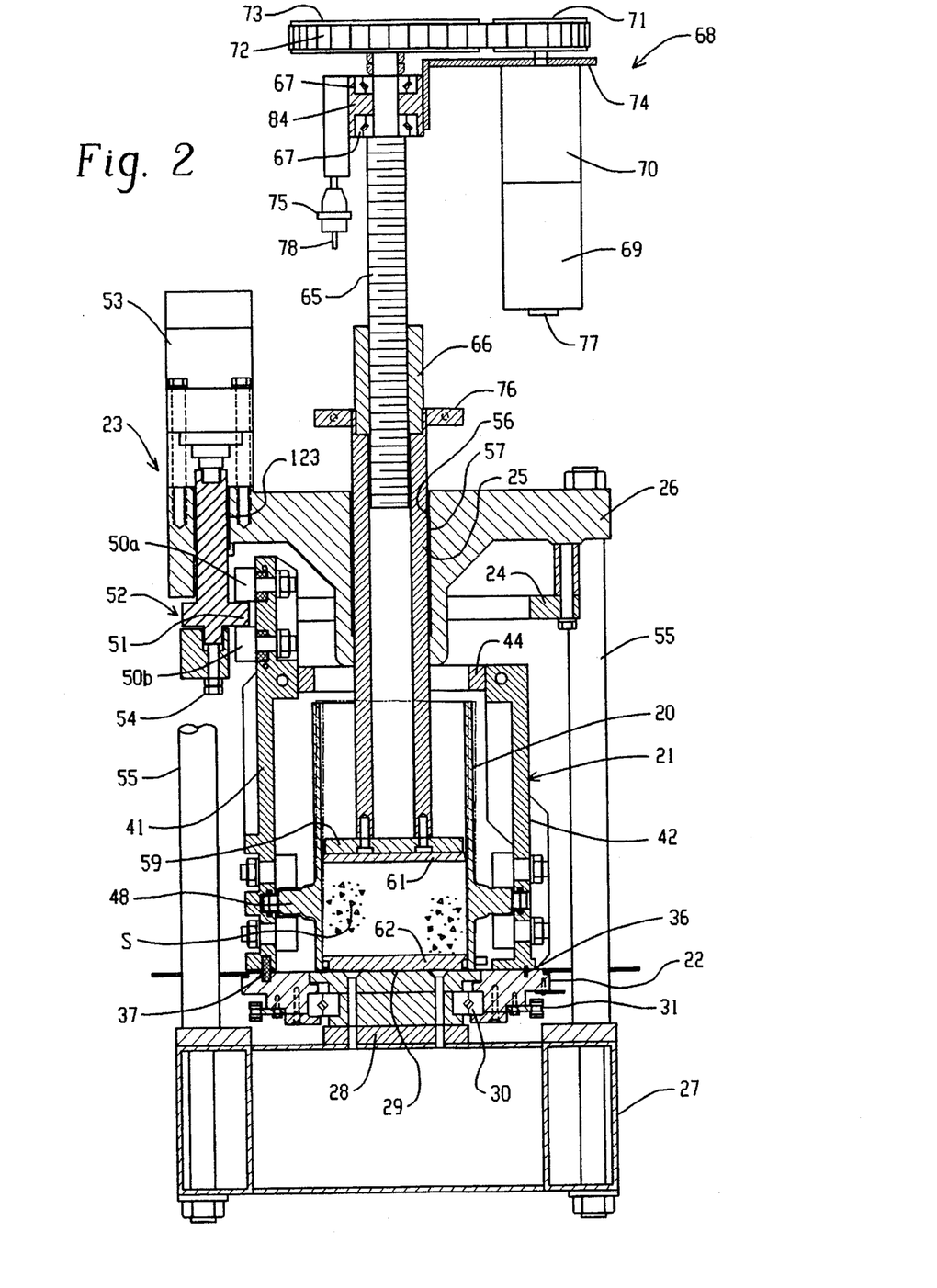
FIG. 2 is a partial cross-sectional side view of the compacting portion of the gyratory compactor of the present invention with the cabinet wall removed.

FIG. 2 illustrates in cross-section the specimen compacting portion of the gyratory compactor housed in upper portion 15. In general, the major components of the compacting portion of the apparatus include a generally cylindrical mold 20 (into which a material specimen S is placed) surrounded by a mold carriage assembly 21 connected at a bottom end to a circular rotation base 22 and in roller guided contact at a top end with a mold carriage tilt link assembly 23 for aligning upper rollers of the mold carriage assembly for rotation about a fixed ring 24. A ram 25 is positioned vertically through a guide frame 26 for insertion into mold 20 to compress material specimen S.

A base frame 27 (connected to frame 11 of lower portion 13 of FIG. 1) supports a mold base 28 which provides a horizontal surface 29 upon which the mold 20 is placed during gyratory compaction of material in the mold. The mold base 28 supports and is encircled by a rotation base bearing 30 connected to circular rotation base 22. The rotation base bearing 30 may be for example a crossed roller bearing of sufficient load rating to withstand the reaction force through the mold carriage at maximum gyration rpm of a fully loaded mold as described below.

Figure 3:
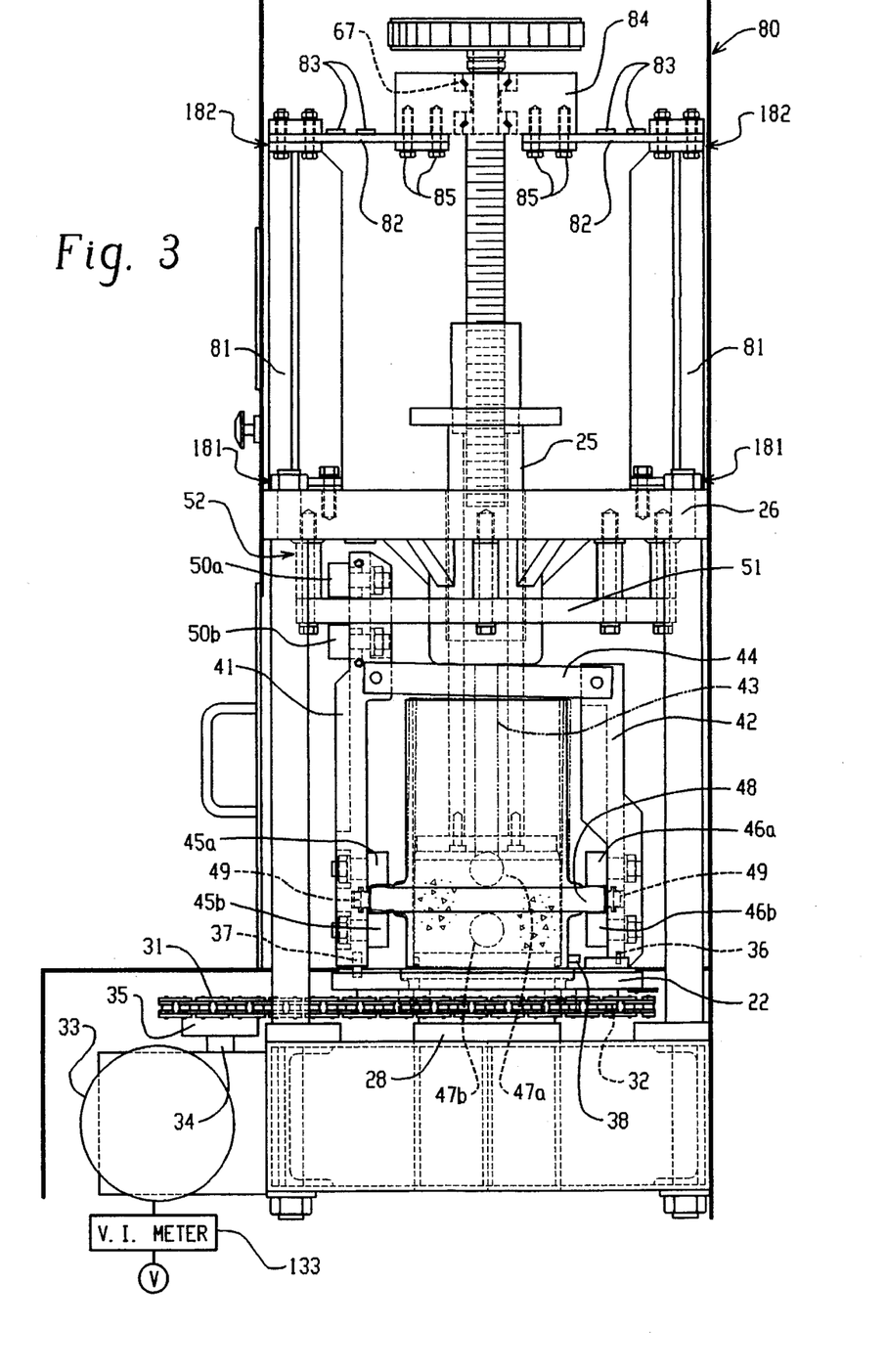
FIG. 3 is a partial cross-sectional view of the mold carriage assembly of the present invention.

As further illustrated in FIG. 3, a drive chain 31 engaging a sprocket 32 attached to rotation base 22 (parallel to the plane of rotation) rotationally drives rotation base 22 upon rotation base bearing 30 about mold base 28. An electric drive motor 33 is powered to rotate shaft 34 to rotate drive sprocket 35 in engagement with drive chain 31. By attachment of a bottom end of mold carriage assembly 21 to rotation base 22 (by fasteners 36 and pins 37), the chain driven rotation of mold base 28 rotates the entire mold carriage assembly 21 around mold 20, without rotating mold 20.

Figure 4:
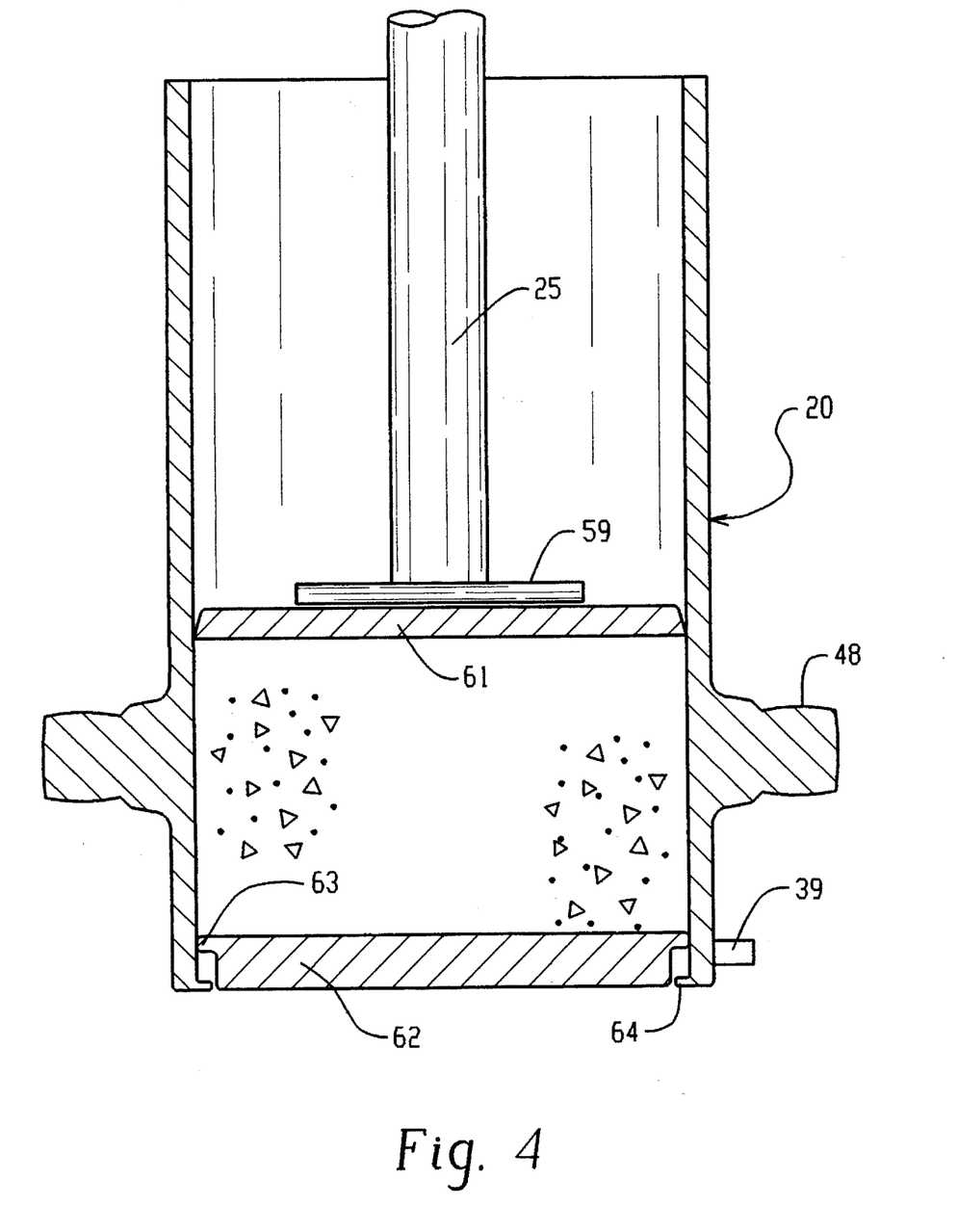
FIG. 4 is a cross section of the mold of the present invention with a compaction ram inserted in the mold.

A chuck 38 may be provided to protrude upward from horizontal surface 29 of mold base 28 to contact a key 39 extending from the side of mold 20 (as shown in FIG. 4) to insure against any frictionally induced rotation of mold 20 during gyration which would interfere with testing requiring an exact number of gyrations.

The primary function of mold carriage assembly 21 is to gyrate the vertical axis of the mold 20 about the vertical axis of the ram 25 during compaction of material in the mold by the ram. As best shown in FIG. 2, mold carriage assembly 21 includes at least two vertical members 41 and 42, suspended by through pin attachment from a mold carriage ring 44 at opposing points on the ring. A third vertical member 43 (shown in phantom in FIG. 3) may also be provided equidistant from members 41 and 42 to maintain intersection of the vertical axis of the mold with the apex of gyration and precisely maintain the angle of gyration during rotation of rotation base 22. Vertical members 41 and 42 and 43 each support, by horizontal journalled bearings, parallel vertically spaced apart mold roller sets 45a and 45b, 46a and 46b and 47a and 47b, respectively, which receive and support a radial flange 48 attached to and extending horizontally from the outer periphery of mold 20. Each vertical member may also have a vertically mounted roller 49 placed between each of the spaced apart roller sets for rolling contact with the outer peripheral face of radial flange 48 of mold 20 to reduce wear and friction of the mold during gyration.

To offset the vertical axis of the mold 20 within the mold carriage assembly to a selected gyration angle, vertical member 41 serves as mold carriage lift link, having an upper set of parallel spaced apart rollers 50a and 50b straddling a ring section 51 of a lift link 52 of the mold carriage tilt link assembly 23. Because ring section 51 constitutes a radial section of fixed ring 24, upper rollers 50 can travel about fixed ring 24 only when lift 52 is raised to align ring section 51 in the same plane as fixed ring 24. Lift link 52 is actuated to perform this alignment function by, for example, a hydraulic cylinder 53, which can be optionally equipped with a self-locking check valve. With fixed ring 24 positioned in a plane parallel to horizontal surface 29 of mold base 28, lifting of vertical member 41 by mold carriage tilt link assembly 23 to align ring section 51 with fixed ring 24, the vertical axis of the mold 20 in the mold carriage is tilted to a gyration angle as determined by the length of vertical member 41. Driven rotation of rotation base 22 rotates the mold carriage 21 and roller sets 45, 46, 47 about radial flange 48 of the mold, and upper roller set 50 about fixed ring 24. Roller sets 45 and 47, being partially lifted by the tilt link assembly, position radial flange 48 of mold 20 in a plane not parallel to horizontal surface 29, i.e., with the vertical axis of the mold positioned at an angle out of co-axial alignment with the vertical axis of the ram (as indicated in FIGS. 2 and 3) thereby positioning the mold for gyration about the foot of the ram.

Figure 5A:
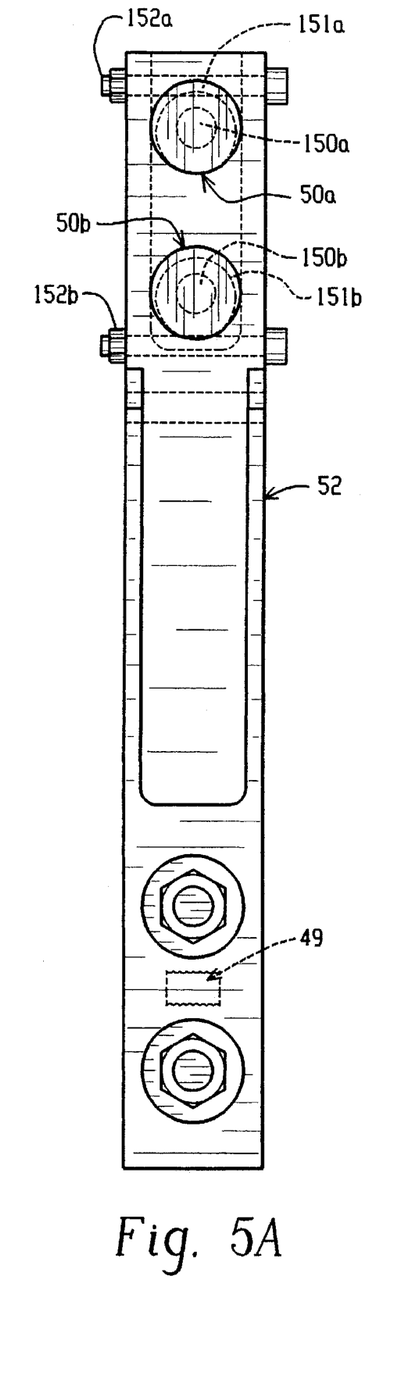
FIG. 5A is a side view of an adjustable lift link assembly of the mold carriage of the present invention, taken in the direction of the arrows 5A—5A in FIG. 5B.
Figure 5B:
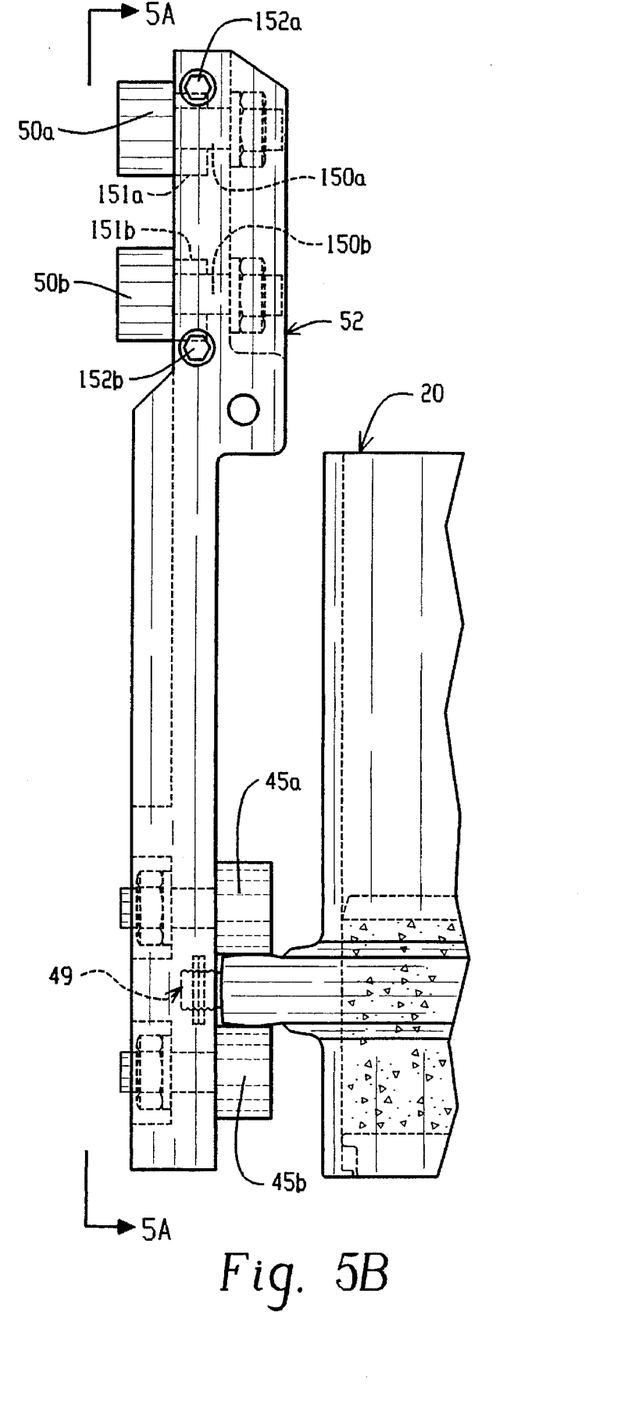
FIG. 5B is a front view of the adjustable lift link assembly of the present invention.

To enable fine adjustment of the gyration angle of the mold within the mold carriage assembly after alignment of ring section 51 with fixed ring 24, vertical member 41 can be adapted to include axis adjustable mounting of upper roller set 50 to selectively adjust the distance between the axes of upper roller set 50 and lower roller set 45. As shown in FIGS. 5A and 5B, shafts 150a and 150b of upper rollers 50a and 50b are each eccentrically mounted within respective cams 151a and 151b, each having worm-screw threads about their periphery and mounted within lift link 52 to be in threaded engagement with corresponding cam adjustment worms 152a, 152b also mounted within lift link 52 transverse to the axes of cams 151.

In operation, for example to change the distance between the axis of upper roller 50a and lower roller 45a, cam adjustment worm 152a is turned to rotate by worm screw engagement cam 151a which carries the axis of upper roller shaft 150a about a circular path offset for example one eighth of one inch from the axial center of cam 151a. Cam adjustment worm 152b is then turned to rotate cam 151b to bring roller 50b into contact with the underside of fixed ring 24.

Fine pitch threads in the worm screw engagement of worms 152 with cams 151 provides for minute positional adjustment of the axes of upper rollers 50 relative to the axes of lower rollers 45 within the range of the offset between axes of the cams and upper rollers. The cam adjustment mechanism therefore provides for fine gyration angle adjustment within, for example, a one and one half degree range provided by the cam/roller axes offset, to adjust and fix the gyration angle of the mold within the mold carriage. An exact gyration angle within the cam adjustment range is determinable by use of a mold jig and clinometer positioned within the mold carriage. When a desired gyration angle is set by worms 152, a hydraulic stop 54 is adjusted and set to define a linear travel distance of lift link 52 (as actuated by hydraulic cylinder 53) which corresponds to the length of vertical member 41 for return of the mold carriage and mold to a zero degree gyration angle position.

As shown in FIG. 2, fixed ring 24 is attached to guide frame 26 positioned and supported above the mold carriage assembly 21 by tie rods 55 connected to base frame 27. Guide frame 26 includes a vertical passage 23 for linearly guiding lift link 52 along its vertical axis as actuated by vertical hydraulic cylinder 53 fixedly mounted to the top of guide frame 26. Guide frame 26 further includes a central vertical passage 56 lined with a ram sleeve bearing 57 for receiving and guiding a ram 58 linearly along a vertical axis into the open top of mold 20. A ram foot 59, of a diameter less than the internal diameter of mold 20, is attached to the axial end of ram 25 inserted into the mold for compressive contact with a mold top plate 61 which is placed directly on top of the material specimen S in the mold. The diameter of ram foot 59 may be less than the diameter of mold top plate 61 which, in addition to insulating a heated material specimen from heat loss, acts to evenly distribute the compressive consolidation force of the ram foot across the width of the specimen in the mold. The diameter of the mold top plate 61 is preferably made to close tolerance with the internal diameter of the mold, to cover the entire specimen with only minor contact of the edges of the mold top plate with the interior walls of the mold during gyratory compaction. By this arrangement, the smaller diameter of the ram foot avoids contact of the peripheral edges of the ram foot with the walls of the mold during gyration. The ram foot 59 is detachable from the end of the ram for exchange with a smaller diameter ram foot used in connection with a smaller diameter mold. Molds of different cavity dimensions (diameters) can be used with the compactor provided the radial flange 48 is a constant diameter to fit within the roller sets of the mold carriage.

As shown in FIG. 4, the material in the mold is compacted by the ram foot 59 and the mold top plate 61 against a removable mold bottom plate 62 which is retained in the bottom of the mold 20 by contact of a radial flange 63 of mold bottom plate 62 with an annular lip 64 projecting radially inward at the bottom of mold. This structure, in combination with the position of radial flange 48 relative to the mold, optimizes the geometry near the bottom of the mold where the majority of compaction takes place, allowing the mold to gyrate about the mold bottom plate 62 which remains flush upon horizontal surface 29 as shown in FIG. 3, thus minimizing relative motion and wear between the mold bottom plate 62 and horizontal surface 29 of mold base 28. Hard self-lubricating surfaces are used on the interfacing areas of the mold assembly to reduce wear.

Referring again to FIGS. 2 and 3, ram 25 is driven linearly along its vertical axis by a lead screw 65 threaded through a lead screw nut 66 fixed to a top end of ram 25. The top end of lead screw 65 is supported and journalled to rotate within lead screw thrust bearings 67 mounted within a block 84 supported by an upper frame portion indicated in FIG. 3 generally at 80. A lead screw drive assembly, indicated generally at 68, includes an electric stepping motor 69, such as Model #UPD 5913 manufactured by Oriental Motor Corporation U.S.A., coupled to a gear reducer unit 70 which is supported by a bracket 74 attached to block 84. A drive gear 71 is attached to a shaft output of gear reducer unit 70 and engaged by a toothed drive belt 72 also engaged with a lead screw drive gear 73 attached to the top end of the lead screw above lead screw thrust bearings 67. A linear position sensor 75, such as for example a linear potentiometer, is mounted to block 84 for positioning proximate and parallel to the lead screw. A ram position indicator arm 76 extending laterally from the top end of the ram 25 moves the mechanical slide 78 of the potentiometer which provides an electrical signal to the control circuitry indicating a home position of the ram. A rotary encoder 77 connected to stepping motor 69 provides (through a control system described below) a digital indication of linear travel of the ram according to the known pitch of the lead screw. By feedback loop control of power to stepping motor 69 as described below, the linear position of the ram foot relative to horizontal surface 29 of mold base 28 can be precisely determined, controlled and monitored. This allows the compactor to be programmed to, for example, compact a specimen to a predetermined height which corresponds to a calculated desired air void (i.e., density).

The upper frame portion 80, which supports the lead screw drive assembly 68, block 84 and thrust bearings 67, is constructed as an integral part of the entire frame structure of the compactor. As shown in FIG. 3, upper frame portion 80 includes vertical members 81 secured at a bottom end 181 to the top of guide frame 26 and supporting at a top end 182 outboard ends of horizontal load beams 82 attached at inboard ends to block 84 by fasteners 85. Load beams 82 are designed to flex in response to the stresses which result when force is applied by the ram to a specimen in the mold. Redundant strain gauges 83 are applied to surfaces of load beams 82 to detect the strain which results from deflection of the load beams in response to the force being applied by the ram. The relative positions of the block 84, as supported by load beams 82, and the lead screw drive assembly 68, as supported by bracket 74 attached to block 84, in combination with the placement of strain gauges 83 upon surfaces of load beams 82, is designed to minimize the effect of the reactive forces from the lead screw drive assembly upon accurate measurement by the strain gauges of the linear force of the ram. Strain gauges 83 provide an analog signal indicative of the magnitude of deflection of the beams and, correspondingly, the axial force of the ram foot upon the specimen. By operation of the feedback loop control system described below, data received from strain gauge measurements is used to determine pulse application to stepping motor 69 to, for example, maintain a constant consolidation pressure of the ram upon the specimen, or otherwise control ram pressure or position in any mode desired.

The amount of energy required to gyrate and compact aggregate asphalt mixes varies dependent in part upon the viscosity of the asphalt oil and the type and shape of mixed aggregate. Therefore, a measurement of an amount of energy required to gyrate an aggregate asphalt mix sample undergoing compaction can yield useful data on physical properties of the asphalt mix. To enable measurement of an amount of energy required to gyrate the mold about the compacting ram, sensors may be provided in the mold base drive train assembly. For example, a power measurement device 133 such as a watt meter, capable of measuring voltage and current, may be provided at the power input to electric drive motor 33 to provide a measurement of an amount of power input to the motor. The analog value of this measurement can then be calibrated by an absorption dynamometer (such as a prony brake which applies a known frictional load) to factor out mechanical losses in the system to yield an accurate value of an amount of effort required to gyrate the mold in the gyratory compaction process.

Figure 6:
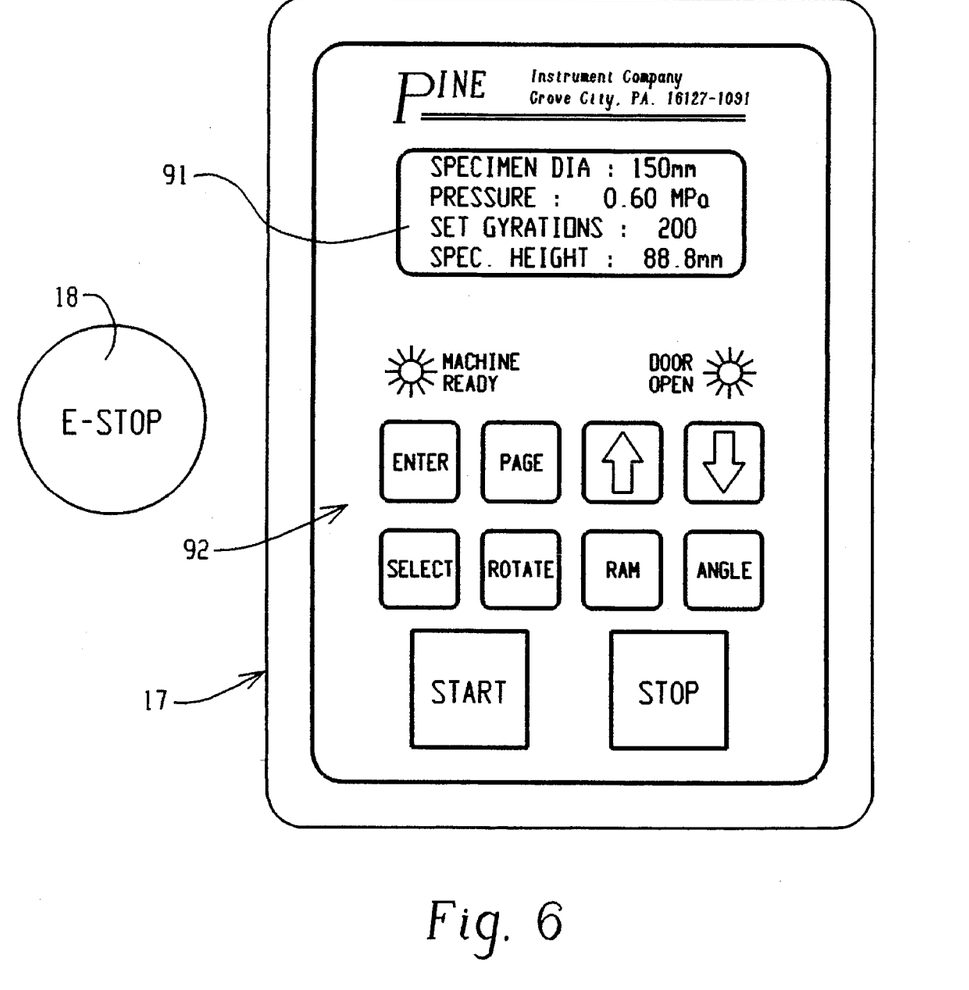
FIG. 6 is an illustration of the control panel layout of the gyratory compactor of the present invention.

A fully integrated interactive computer control system is provided to control the parameters of the various operations of the gyratory compactor. FIG. 6 illustrates the face of control panel 17 as mounted on the exterior of the compactor, which includes a screen display 91, such as an illuminated liquid crystal display, multiple touch pad entry keys 92 including START and STOP functions, and indicator lights such as "MACHINE READY" and "DOOR OPEN". As set forth in Table I, representative testing parameters and functions which can be input through the control panel include rotation of the mold carriage (by powered rotation of the mold base for example to a home position where the mold carriage opening between vertical members 41 and 42 is aligned with access door 16), manual control of ram position, actuation of the mold carriage tilt link assembly to adjust the mold to the desired gyration angle, consolidation pressure, specimen size, and number and rate (rpm) of gyratory revolutions.

TABLE I

| Key | Action |
| --- | --- |
| Page + ↑ | Moves to other options menu |
| Page − ↓ | Exits other option menu |
| Select | Selects parameter to be changed (value flashes) |
| ↑ or ↓ | Used to change value of flashing parameter |
| Enter | Stores changed parameters |
| Rotate | Display rotational status |
| Rotate & ↑ or ↓ | Rotates mold carriage |
| Ram | Display ram status |
| Ram & ↑ or ↓ | Move ram up or down |
| Angle | Display mold carriage angle status |
| Angle & ↑ or ↓ | Toggles between 0 and gyration angle |
| Start | Starts test sequence |
| Stop | Pauses test |
| Enter and start | Automatic machine parking |

In an automated mode, control system software automatically calculates the force required to produce the desired consolidation pressure on the specimen being compacted.

Data on compaction progress is then displayed on screen 91. Once an automated test routine is started parameters may be viewed but not changed. Data from the previous five (5) compaction tests is stored in volatile memory for purposes of, for example, producing a printout such as represented by FIG. 7, showing specimen height vs. gyration number for one compaction run and, in columnar form at the bottom additional data such as specimen size, ram pressure, etc. Of course all such data could be arranged in any chosen format.

Figure 8A:
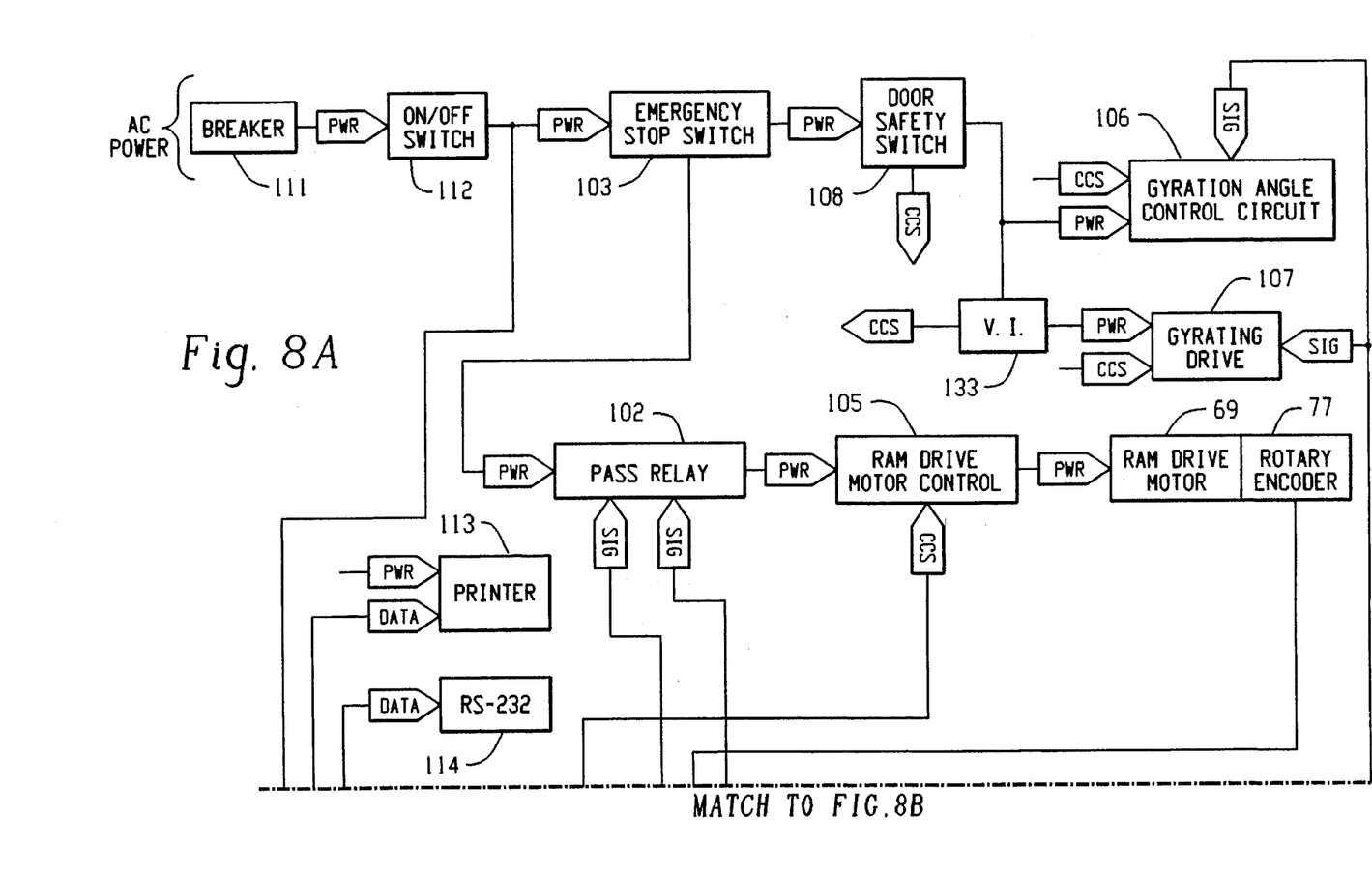
Figure 8B:
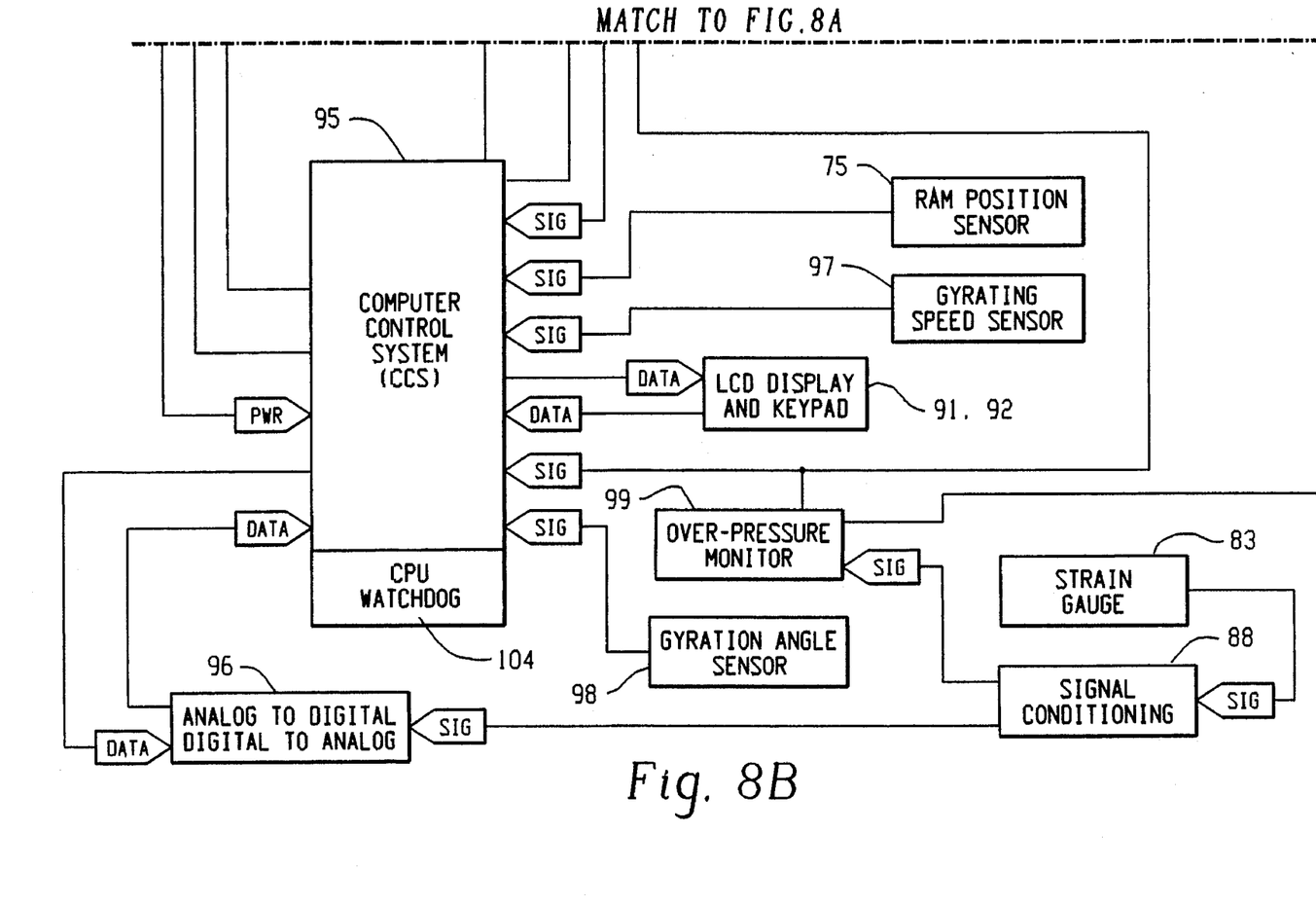

FIG. 8 sets forth a simplified control diagram of the power and control system of the gyratory compactor which includes a central computer control system (CCS) 95 (including a CPU 104) for receiving and processing signals and data to control the operations of the compactor. For example, amplified signals from strain gauges 83 are sent through signal conditioner 88 for conversion to digital form by an A/D converter 96 for input into the CCS 95. The CCS uses this data, for example, to generate a signal to a ram drive motor control 105 to ram drive motor 69 to maintain a constant consolidation pressure exerted by the ram foot on the specimen within a preselected range by use of a modified proportional-integral-derivative algorithm which calculates the required output for the ram drive motor. The CCS also receives signals from rotary encoder 77 on the ram drive motor to generate a signal representing the corresponding ram movement and rate of movement for output to display 91. By counting the signals of the rotary encoder relative to a ram position detected by ram position sensor 75, the CCS can also determine the position of the ram foot from the horizontal surface of the mold base. Other inputs to the CCS include signals from a gyrating speed sensor 97, such as an optical sensor mounted proximate to the mold carriage, signals from a gyration angle sensor 98, and data signals input through control panel keypad 92. An over-pressure monitor 99 detects signals measured at the flexible portion of the frame which are beyond pre-specified parameters, such as would be detected with a firm object under the ram foot, to instruct the CCS to suspend further linear advancement of the ram by a signal to master pass relay 102. A gyration angle control circuit 106 and gyrating drive power controller 107 also receive a signal from over-pressure monitor 99 in the event of excessive ram force to prevent change of gyration angle and gyration of the mold during this condition to avoid damage to the machine. The magnitude of power supplied to the gyrating drive is measured by watt meter 133 which sends readings to the CCS. A door safety switch 108 disables power to the machine through the CCS to suspend all mechanical movement whenever the door 16 is open. AC power is supplied to the machine through a breaker 111 and switch 112. Data acquired by the CCS is output through appropriate ports to printer 113 and/or other peripheral device such as a monitor (not shown) through, for example, an RS-232 interface 114.

Accurate ram force data can be acquired and processed by the CCS by calibration of the compactor with a separate calibration kit. A preprogrammed calibration routine is reached through a special key sequence to prevent inadvertent use. This user friendly routine will allow a skilled technician to calibrate the machine with a minimum amount of training. Parameters calibrated include consolidation pressure as determined by ram force, specimen height, gyration angle, and the speed of gyration. Manual control of the system allows simple verification of calibrations without actual calibration of the compactor. Calibration data and date are stored in non-volatile computer memory. A precision non-contact tachometer can be used to verify the speed of gyration.

The linear force of the ram foot is calibrated with a ring dynamometer. The calibration routine prompts the operator to load the ring to a specific force, e.g., 2000N. The operator manually controls the ram to apply that force, as indicated by the ring dynamometer, and then presses "Enter". The CCS stores the required information and prompts the operator for the next predetermined load, and the process is repeated until the full range of the compactor has been calibrated. The operator may verify any of the calibrations before continuing by, for example, reapplying the force to the ring dynamometer. The calibration sequence will follow ASTM E4-89 procedures.

After the consolidation force has been calibrated over the entire force range of the machine, the operator follows a similar process to calibrate specimen height. The control system prompts the operator to insert a precision gauge block under the ram foot. The block is then loaded throughout the full force range applied by the ram foot, as may be automatically controlled by the CCS. Several gauge blocks are used to calibrate specimen height for the full range of ram travel. By loading through the entire operating range of the compactor while a gauge block is under the ram foot, accurate data on the internal frame deflection is obtained and recorded. The several gauge blocks representing different ram positions are use to create a matrix of data for compactor frame deflection at various loads and ram extension positions. This data is stored and utilized by the CCS during normal operation to eliminate errors in measurement due to compactor frame deflection.

Multiple safety features, such as an emergency stop switch, are incorporated into the design of the gyratory compactor including a completely enclosed compacting chamber which conceals all moving parts and pinch points. Compacting chamber access door 16 is provided with a lockout switch which disables the tilt, rotation and ram movement when the door is open. This lockout switch further utilizes a special keyed actuator which makes disabling of the switch difficult. The CCS monitors the status of the door and a light on the control panel indicates when the door is not latched. A window in the door allows the operator to view the compacting chamber.

The compactor further includes operation protection features integral to the control system to prevent or minimize damage to the compactor in the event of a failure. The over-pressure circuitry described in connection with FIGS. 8A and 8B monitors the force of the ram independent of the software to ensure that the compactor is operating within its rated capacity. The compactor is structurally designed with inherent flexibility to withstand an overload of more than twice the maximum compacting force of the ram without damage. Limit switches are provided to indicate ram positions beyond normal travel. The control system can shut down the compactor through a master pass relay circuit 102 (shown in FIG. 8A and 8B), as can the emergency stop switch 103 in the event of a potentially damaging condition. Independent circuitry (CPU watchdog 104) is provided to monitor the operation of the CCS to ensure proper function. The CCS can be programmed to generate error messages to aid in trouble shooting to quickly determine the cause of any problem. All critical systems have a built-in redundancy to prevent damage should a single failure occur.

By use of the above-described apparatus, a compacted specimen of hot mix asphalt (HMA) material (e.g., asphalt mixed with an aggregate material such as crushed stone) can be produced by loading a mold with a quantity of HMA material, placing the mold top plate on top of the material in the mold and putting the entire mold assembly into an oven for pre-compacting heating to a specified temperature, removing the mold assembly from the oven and placing it in the compacting chamber in position within the mold carriage. With the computer control system preprogrammed with testing parameters for constant compaction (consolidation) ram pressure, angle of gyration, number and rate of gyration or final specimen height within the mold (according to a predetermined air void percentage), the operator simply presses the start button and the CCS initiates the test routine by running the ram to contact with the mold top plate, tilting the mold carriage to the gyration angle, and commencing gyration and compaction at the specified rates. At completion of the test the mold carriage is actuated to return the mold to a zero degree gyration angle to square the specimen within the mold. The ram is then retracted to a home position to allow removal of the mold from the compactor. The mold is transferred, for example by sliding without lifting, upon surface A into position in mold positioning extruder brackets 122 for power-assisted extrusion or extraction of the specimen from the mold by extruder 19 which, by operation of hydraulic hand pump 109 or electric screw jack assembly 130, drives a cylinder or screw or extruder rod vertically upward against the mold bottom plate to push the specimen out of the open top of the mold.

Although the invention has been shown and described with respect to certain preferred embodiments, certain variations and modifications may occur to those skilled in the art. For example, many different types of motors and drive assemblies could be used to drive the various components of the gyratory compactor in connection with the computer control system to achieve constant consolidation compaction pressure at an exact gyration rate. The apparatus may be used to test materials other than asphalt and asphalt aggregates. The apparatus may also be used to perform applied force testing other than compaction or gyratory compaction. All such variations and modifications of the apparatus and method are within the purview of the present invention notwithstanding the defining limitations of the accompanying claims and equivalents thereof.

We claim:

1. A materials testing apparatus for subjecting a material to forces comprising, in combination,
   a frame having a mold supporting surface for supporting a mold, a mold carriage, mold carriage rotation means, a mold carriage tilt link assembly, a ram, and a ram driving assembly,
   said mold having a cavity for containing a quantity of said material,
   said mold in contact with said mold carriage,
   said mold carriage further connected to said mold carriage tilt link assembly, said mold carriage tilt assembly operative to lift a portion of said mold carriage to tilt and fixedly position a vertical axis of said mold within said mold carriage,
   means for rotating said mold carriage about said mold,
   a material compaction ram connected to a ram driving assembly, said ram drivingly insertable into said mold to exert a compressive force upon said material within said mold while said mold carriage is rotated about said mold, and
   a mold material extruder supported by said frame, said mold material extruder having means for driving a vertically oriented extruder rod upward from said mold supporting surface.

2. The apparatus of claim 1 wherein said mold material extruder comprises a hydraulic cylinder operatively connected to drive said vertically oriented extruder rod.

3. The apparatus of claim 1 wherein said mold material extruder comprises an electrically powered screw jack operatively connected to drive said vertically oriented extruder rod.

4. The apparatus of claim 1 wherein said mold material extruder is positioned within said frame adjacent to said mold carriage.

5. The apparatus of claim 1 further comprising mold extruder positioning brackets extending from the mold supporting surface.

6. A gyratory compaction apparatus for compacting a material held in a mold as the mold is gyrated, the apparatus comprising:
   a frame,
   a mold supporting surface upon the frame,
   a mold for receiving material to be compacted,
   a power driven compaction ram for compacting material in the mold by insertion of the ram into the mold,
   a mold gyrator for gyrating the mold as the compaction ram is inserted into the mold, and
   a material extractor for extracting compacted material from the mold, the material extractor having a mold supporting surface and a vertically oriented rod powered to rise vertically from the mold supporting surface of the frame to extract material from a mold.

7. A gyratory compactor apparatus for subjecting a material to forces, comprising:
   a frame having a first mold supporting surface, a mold gyrating assembly, a ram and a ram drive assembly,
   said mold having a mold cavity for receiving a quantity of said material,
   said mold further having an open top and a closed bottom,
   a ram supported by said frame and insertable into said mold cavity through said open top of said mold to compact said material in said mold, and
   a mold gyrating assembly in contact with said mold and operative to gyrate a vertical axis of said mold relative to a vertical axis of said ram as said ram is inserted and driven into said mold cavity, and
   a mold material extractor having a second mold supporting surface in a same horizontal plane with the first mold supporting surface, mold positioning brackets attached to the second mold supporting surface, and a vertically oriented extractor rod operative to rise from said second mold supporting surface into said mold to extract material from said mold.

8. The gyratory compactor apparatus of claim 7 wherein said mold is in the form of a cylinder having a flange extending radially from an outer periphery of said cylinder, the apparatus further comprising mold positioning brackets which extend from said second mold supporting surface and engage said flange to position and hold said mold for insertion of said extractor rod.

9. A gyratory compactor apparatus for compacting a specimen of material while said specimen is gyrated, said apparatus comprising, in combination,
   a mold for holding said specimen,
   a mold support structure for supporting said mold,
   a compacting ram positioned and driven for insertion into said mold to compact said specimen within said mold,
   a mold gyrating assembly in contact with said mold and powered to gyrate said mold while said compacting ram is inserted and driven into said mold and,
   a mold extractor for extracting material from said mold.

10. A material compaction apparatus comprising:

a mold for receiving a material to be compacted, a mold supporting frame, a compaction ram driving assembly connected to a compaction ram positioned for insertion into the mold, a mold gyrating mechanism in contact with the mold, and a mold material extruder assembly for removing compacted material from the mold, the extruder assembly comprising a mold supporting surface in a common plane on which the mold is supported by the mold supporting frame, a mold bracket on the mold supporting surface which positions and secures the mold over a vertically oriented extrusion ram powered to rise from the mold supporting surface into the mold to extrude material from the mold.

11. A materials testing machine having a first mold supporting surface proximate mold gyration and compaction machinery, and a second mold supporting surface proximate mold positioning brackets and a mold specimen extruder, said mold gyration and compaction machinery including a mold gyrating mechanism which gyrates a vertical axis of the mold and a compaction ram insertable into the mold as the mold is gyrated, and said mold specimen extruder including a vertically oriented extrusion rod powered to rise from the second mold supporting surface into a mold.

12. A combined gyratory compactor and mold extruder assembly comprising:

a frame which supports a mold gyration assembly and a first mold supporting surface, a mold for holding material to be compacted, a mold gyrator and a compaction ram, a second mold supporting surface, and a mold specimen extruder having an extrusion rod positioned and powered to rise from the second mold supporting surface.

* * * * *

UNITED STATES PATENT AND TRADEMARK OFFICE
CERTIFICATE OF CORRECTION

PATENT NO. : 5,606,133
DATED : February 25, 1997
INVENTOR(S) : Hines, et al.

It is certified that error appears in the above-indentified patent and that said Letters Patent is hereby corrected as shown below:

Page 1, line 10, please insert --

<u>Related Applications</u>

This application is a continuation-in-part of application serial number 08/198,497, now U.S. Patent No. 5,456,118, issued October 10, 1995.--

Signed and Sealed this

Twenty-sixth Day of August, 1997

Attest:

BRUCE LEHMAN

Attesting Officer

Commissioner of Patents and Trademarks